US00PP27483P2

(12) United States Plant Patent
Koppe

(10) Patent No.: US PP27,483 P2
(45) Date of Patent: Dec. 20, 2016

(54) ***BEGONIA* PLANT NAMED 'KRBELLE01'**

(50) Latin Name: ***Begonia hybrida*×*Begonia bowerae***
Varietal Denomination: KRBELLE01

(71) Applicant: Lubbertus H. Koppe, Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 14/545,699

(22) Filed: Jun. 6, 2015

(51) Int. Cl.
*A01H 5/02* (2006.01)

(52) U.S. Cl.
USPC ..... Plt./343

(58) Field of Classification Search
USPC ..... Plt./343
CPC ..... A01H 5/0238
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'KRBELLE01' characterized by its upright, outwardly spreading and mounded plant habit; moderately vigorous growth habit; dense and bushy appearance; and yellow green-colored leaves with dark brown-colored margins.

2 Drawing Sheets

Botanical designation: *Begonia hybrida*×*Begonia bowerae*.

Cultivar denomination: 'KRBELLE01'.

BACKGROUND OF THE INVENTION

The present invention relates to a new and distinct cultivar of *Begonia* plant, botanically known as *Begonia hybrida*× *Begonia bowerae* and hereinafter referred to by the name 'KRBELLE01'.

The new *Begonia* plant is a product of a planned breeding program conducted by the Inventor in Ermelo, The Netherlands. The objective of the breeding program is to create new types of *Begonia* plants with unique and attractive foliage.

The new *Begonia* plant originated from a cross-pollination made by the Inventor in Ermelo, The Netherlands in March, 2004 of *Begonia hybrida* 'Cleopatra', not patented, as the female, or seed, parent with an unnamed proprietary selection of *Begonia bowerae*, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in March, 2005.

Asexual reproduction of the new *Begonia* plant by leaf cuttings taken in a controlled greenhouse environment in Ermelo, The Netherlands since July, 2005 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRBELLE01'. These characteristics in combination distinguish 'KRBELLE01' as a new and distinct *Begonia* plant:

1. Upright, outwardly spreading and mounded plant habit.
2. Moderately vigorous growth habit.
3. Dense and bushy appearance.
4. Yellow green-colored leaves with dark brown-colored margins.

Plants of the new *Begonia* differ primarily from plants of the female parent, 'Cleopatra', in leaf color as plants of 'Cleopatra' have dark brown-colored leaves.

Plants of the new *Begonia* differ primarily from plants of the male parent selection in leaf color as plants of the male parent selection have dark green-colored leaves.

Plants of the new *Begonia* can be compared to plants of *Begonia bowerae* 'Tiger', not patented. In side-by-side comparisons conducted in Ermelo, The Netherlands, plants of the new *Begonia* differed primarily from plants of 'Tiger' in leaf color as plants of 'Tiger' had green-colored leaves with brown-colored spots.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRBELLE01' grown in a container.

The photograph on the second sheet are close up views of the upper (left) and lower (right) surfaces of typical leaves of 'KRBELLE01'.

DETAILED BOTANICAL DESCRIPTION

The aforementioned photographs and following observations and measurements describe plants grown during the winter in 13-cm containers in a shaded glass-covered greenhouse in Ermelo, The Netherlands and under cultural practices typical of commercial *Begonia* production. During the production of the plants, day temperatures averaged 20° C. and night temperatures averaged 18° C. Plants were twelve weeks old when the photographs and description were taken. In the following description, color references are made to The Royal Horticultural Society Colour Chart, 2007 Edition, except where general terms of ordinary dictionary significance are used.

Botanical classification: *Begonia hybrida*×*Begonia bowerae* 'KRBELLE01'.

Parentage:

*Female, or seed, parent.*—*Begonia hybrida* 'Cleopatra', not patented.

*Male, or pollen, parent.*—Unnamed proprietary selection of *Begonia bowerae*, not patented.

Propagation:

*Type.*—By leaf cuttings.

*Time to initiate roots, summer and winter.*—About 20 days at temperatures about 20° C.

*Time to produce a rooted young plant, summer and winter.*—About two months at temperatures about 20° C.

*Root description.*—Fine, fibrous; white to orange brown in color.

*Rooting habit.*—Freely branching; medium density; plants of the new *Begonia* have not been observed to form tubers.

Plant description:

*Plant habit and form.*—Upright, outwardly spreading and mounded plant habit; overall plant shape, flattened globular.

*Growth habit.*—Moderately vigorous growth habit and moderate growth rate; suitable for 12-cm and larger containers; under optimal environmental and cultural conditions, usually about ten weeks are required to produce proportional 13-cm potted plants; leaves grow in basal rosettes; dense and bushy appearance, about twelve basal rosettes develop per plant with about 15 leaves per basal rosette; flower development has not been observed on plants of the new *Begonia.*

*Plant height.*—About 22.3 cm.

*Plant width.*—About 42.5 cm.

*Leaves.*—Arrangement: Alternate, arranged in basal rosettes; simple. Length: About 8.8 cm. Width: About 12.4 cm. Shape: Unequal reniform. Apex: Acuminate. Base: Oblique. Margin: Irregularly dentate to bi-serrate; laciniate. Texture, upper surface: Smooth, glabrous; velvety. Texture, lower surface: Smooth, glabrous; slightly velvety. Luster, upper surface: Matte. Luster, lower surface: Slightly glossy. Venation pattern: Palmate. Color: Developing leaves, upper surface: Close to N144D; margins, close to 183B. Developing leaves, lower surface: Close to N145B; margins, close to 184B. Fully expanded leaves, upper surface: Close to 144A; margins, close to 200A; venation, close to N144B. Fully expanded leaves, lower surface: Close to 139D; margins, close to 187A; venation, close to N144B. Petioles: Length: About 16.6 cm. Diameter: About 5 mm. Texture, upper and lower surfaces: Sparsely pubescent. Glossy, upper and lower surfaces: Moderately glossy. Color, upper and lower surfaces: Close to 145B; lenticels, close to 183B. Stipules: Length: About 1.5 cm. Width: About 8 mm. Shape: Ovate. Apex: Aristate. Margin: Entire. Texture, upper and lower surfaces: Smooth, glabrous. Color, upper and lower surfaces: Close to 145D.

Disease & pest resistance: Resistance to pathogens and pests common to *Begonia* plants has not been observed on plants of the new *Begonia.*

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'KRBELLE01' as illustrated and described.

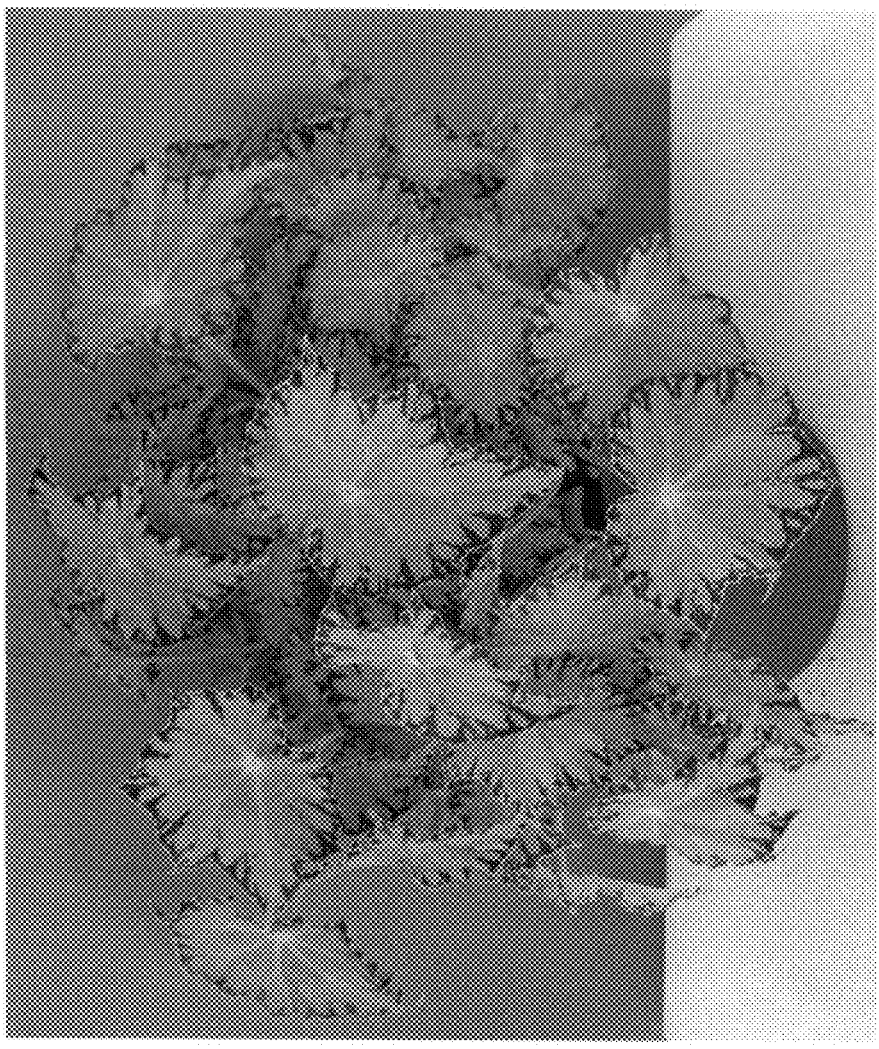

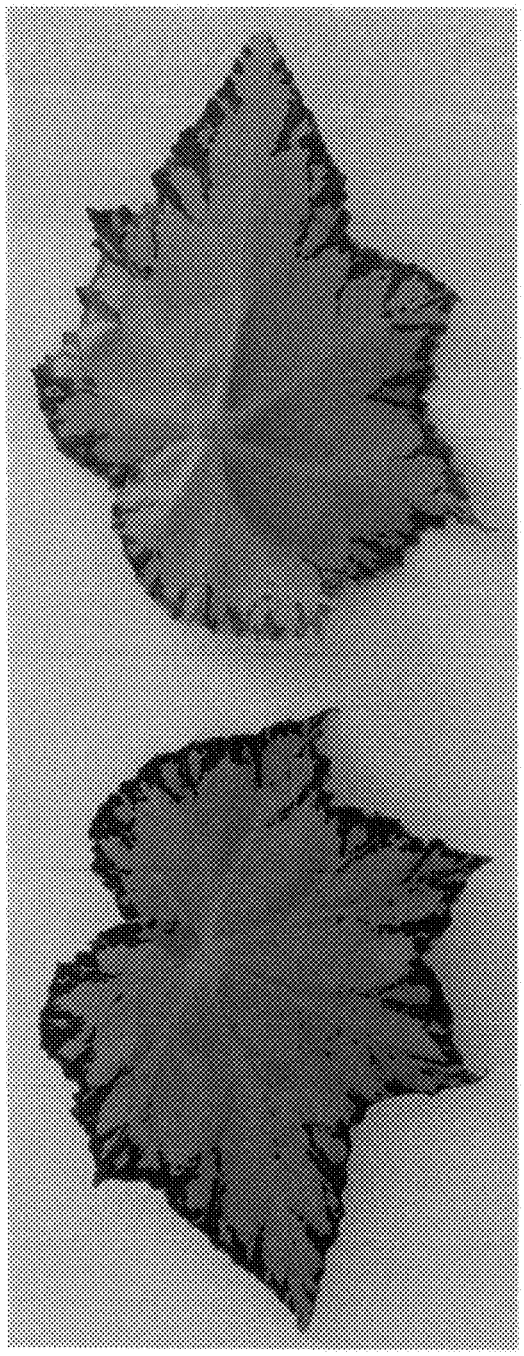

* * * * *